US006949758B2

(12) United States Patent
Shi et al.

(10) Patent No.: US 6,949,758 B2
(45) Date of Patent: Sep. 27, 2005

(54) LCC-BASED FLUID-LEVEL DETECTION SENSOR

(75) Inventors: Zhong-You Shi, Ann Arbor, MI (US); C. Allen Marlow, Saline, MI (US)

(73) Assignee: Visteon Global Technologies, Inc., Dearborn, MI (US)

(*) Notice: Subject to any disclaimer, the term of this patent is extended or adjusted under 35 U.S.C. 154(b) by 285 days.

(21) Appl. No.: 10/265,954

(22) Filed: Oct. 7, 2002

(65) Prior Publication Data

US 2003/0075698 A1 Apr. 24, 2003

Related U.S. Application Data

(60) Provisional application No. 60/330,306, filed on Oct. 19, 2001.

(51) Int. Cl.[7] .................. G01N 15/08; G01N 21/49; G01N 21/85
(52) U.S. Cl. ................ 250/577; 250/574; 250/904; 356/436; 73/293
(58) Field of Search ................ 340/450, 618, 340/619, 555–557, 904; 356/436; 73/293

(56) References Cited

U.S. PATENT DOCUMENTS

| 3,448,616 | A | | 6/1969 | Wostl et al. |
| 3,463,134 | A | | 8/1969 | Zechnall et al. |
| 3,895,612 | A | | 7/1975 | Keely et al. |
| 4,082,959 | A | * | 4/1978 | Nakashima ................ 250/577 |
| 4,132,899 | A | * | 1/1979 | Shigemasa et al. ......... 250/577 |

(Continued)

FOREIGN PATENT DOCUMENTS

| DE | 28 39 127 A1 | 3/1980 |
| DE | 3700832 | 7/1988 |
| DE | 199 26 846 A1 | 12/2000 |
| EP | 0266934 A1 | 5/1988 |
| EP | 0 290 243 | 5/1988 |

(Continued)

OTHER PUBLICATIONS

Combined Search and Examination Report dated Jun. 23, 2003 for corresponding British Patent Application No. GB 0224033.1.
Brian, M., "How Car Engines Work", http://www.howstuffworks.com/engine1.htm, pp. 1–4, 2002.
Nice, K., "How Automobile Ignition Systems Work", httyp://www.howstuffworks.com/ignition–system.htm/printable, pp. 1–9, 2002.
Ofria, C., "A Short Course on Automobile Engines", http://www.familycar.com/engine.htm.
Copy of Search Report dated May 28, 2003 in connection with Application No. GB 0224391.3.
Copy of Search Report dated May 28, 2003 in connection with Application No. GB 0224389.7.

*Primary Examiner*—David Porta
*Assistant Examiner*—Davienne Monbleau
(74) *Attorney, Agent, or Firm*—Brinks Hofer Gilson & Lione

(57) ABSTRACT

A non-mechanical fluid level sensor based on light communication channel (LCC) technology. In a preferred embodiment, one end of the LCC is connected to a signal source while another end is connected to a sensor. The LCC is dipped in a fluid container and a signal propagates and undergoes internal reflection through the LCC towards one of its ends which is connected to the sensor. The fluid level is detected preferably by measuring the intensity of the signal reflected with the LCC that reaches a sensor. Different fluid levels preferably correspond to linearly varying detected signal intensities. A main LCC bus may communicate remotely with the sensor without wiring or other electrical connectors.

13 Claims, 3 Drawing Sheets

U.S. PATENT DOCUMENTS

| | | |
|---|---|---|
| 4,134,639 A | 1/1979 | Di Vita |
| 4,182,935 A | 1/1980 | Chown |
| 4,187,025 A * | 2/1980 | Harmer .................... 356/133 |
| 4,269,152 A | 5/1981 | Van Siclen, Jr. |
| 4,280,751 A | 7/1981 | SiVita |
| 4,311,048 A | 1/1982 | Merz |
| 4,489,602 A | 12/1984 | Henning |
| 4,491,830 A | 1/1985 | Miyabe |
| 4,544,840 A | 10/1985 | Keller |
| 4,674,828 A | 6/1987 | Takahashi et al. |
| 4,745,293 A | 5/1988 | Christensen |
| 4,757,212 A | 7/1988 | Saito |
| 4,789,214 A | 12/1988 | Vilhelmsson et al. |
| 4,817,466 A | 4/1989 | Kawamura et al. |
| 4,851,969 A | 7/1989 | Davenport et al. |
| 4,912,522 A | 3/1990 | Oates et al. |
| 4,928,319 A | 5/1990 | Pitt et al. |
| 4,963,729 A | 10/1990 | Spillman et al. |
| 5,001,642 A | 3/1991 | Botzenhardt et al. |
| 5,077,482 A | 12/1991 | Vali et al. |
| 5,089,696 A | 2/1992 | Turpin |
| 5,214,707 A | 5/1993 | Fujimoto et al. |
| 5,226,090 A | 7/1993 | Kimura |
| 5,247,580 A | 9/1993 | Kimura et al. |
| 5,291,032 A | 3/1994 | Vali et al. |
| 5,328,665 A | 7/1994 | Geiger |
| 5,363,463 A | 11/1994 | Kleinerman |
| 5,380,014 A | 1/1995 | Schäpörkotter |
| 5,384,467 A | 1/1995 | Plimon et al. |
| 5,399,876 A * | 3/1995 | LaClair .................... 250/577 |
| 5,521,992 A | 5/1996 | Chun et al. |
| 5,528,409 A | 6/1996 | Cucci et al. |
| 5,539,200 A | 7/1996 | Lebby et al. |
| 5,659,132 A | 8/1997 | Novak et al. |
| 5,693,936 A | 12/1997 | Komachiya et al. |
| 5,745,611 A | 4/1998 | Komachiya et al. |
| 5,822,099 A | 10/1998 | Takamatsu |
| 5,831,263 A | 11/1998 | Komachiya et al. |
| 5,872,609 A | 2/1999 | Hiji et al. |
| 5,936,235 A | 8/1999 | Minamitani et al. |
| 6,150,734 A | 11/2000 | Neibecker et al. |
| 6,173,609 B1 * | 1/2001 | Modlin et al. ............... 73/293 |
| 6,186,106 B1 | 2/2001 | Glovatsky et al. |
| 6,230,138 B1 | 5/2001 | Everhart |
| 6,240,347 B1 | 5/2001 | Everhart et al. |
| 6,301,030 B1 | 10/2001 | Robinson |
| 6,301,957 B1 | 10/2001 | Sakaguchi et al. |
| 6,320,184 B1 | 11/2001 | Winklhofer et al. |
| 6,357,426 B1 | 3/2002 | Schleupen |
| 6,429,447 B1 * | 8/2002 | Nowak et al. ............. 250/573 |
| 6,538,261 B1 * | 3/2003 | McConnel et al. ........ 250/577 |
| 6,555,837 B2 * | 4/2003 | Benton .................... 250/577 |
| 2001/0019568 A1 | 9/2001 | Sakata |

FOREIGN PATENT DOCUMENTS

| | | |
|---|---|---|
| EP | 0 334 533 | 9/1989 |
| EP | 0 386 965 | 9/1990 |
| EP | 0 454 165 A2 | 10/1991 |
| EP | 0 685 948 A1 | 5/1995 |
| EP | 0 859 479 A2 | 2/1998 |
| EP | 1 026 839 A2 | 1/2000 |
| GB | 2 164 516 A | 3/1986 |
| GB | 2 177 869 A | 1/1987 |
| JP | 59-105730 | 6/1984 |
| JP | 360183630 A | 9/1985 |
| JP | 61-106930 | 5/1986 |
| JP | 2-207204 | 8/1990 |
| JP | 11211517 | 8/1999 |
| WO | WO 90/00296 | 1/1990 |
| WO | WO 89/09324 | 10/1998 |
| WO | WO 00 /77932 A2 | 12/2000 |

* cited by examiner

US 6,949,758 B2

LCC-BASED FLUID-LEVEL DETECTION SENSOR

This application claims the benefit of a U.S. Provisional Application No. 60/330,306 filed on Oct. 19, 2001, which is incorporated herein in its entirety.

FIELD OF THE INVENTION

The invention generally relates to a system for monitoring fluid level. In particular, the invention relates to a system for monitoring fluid level based on a detected light intensity of a signal that propagates through a light communication channel.

BACKGROUND OF THE INVENTION

Various schemes have been developed and used for fluid level detection. Non-optical type sensors such as traditional wired systems have been used widely but they are relatively expensive, usually difficult to assemble, and have several other disadvantages. For example, signals passing through wires often cause cross talking with signal transmission in adjacent wires. Signals passing through wires also cause electromagnetic interference in adjacent wires unless some type of shielding is used. These interferences cause signal distortion.

Optical sensors offer a number of advantages over non-optical sensors. For example, optical sensors do not require electrical contact with the fluid to be monitored. Thus, optical sensors can be fabricated using relatively simple designs. In addition, they are easier to fabricate because they do not have moving parts or components. Also, there exists a variety of materials that may be used for signal transmission that are nonreactive or resistant to the fluid the volume or level of which is to be measured.

On the other hand, while optical fibers are sometimes used in place of wires or incorporated in a molded structure, the use of optical fibers increases the cost of the electronic component system. In addition, integration of optical and electrical components is usually not suited for high volume manufacturing because of difficulties in assembly.

The measurement of the fluid level using optical sensors is typically based on the difference of the indices of refraction of two media that are in contact with each other, e.g., an optical fiber and a fluid in which the optical fiber is immersed, or an optical fiber and the air that surrounds the optical fiber.

The measured intensity of the reflected beam that eventually reaches the sensor depends on the fluid level because a fluid has a different index of refraction from a medium such as air. Because the amount of light that leaks at the interface of two media depends on their relative indices of refraction, different fluid levels give rise to correspondingly different amounts of light that leaks at the interface because, for example, higher fluid levels means a greater portion of a medium such as an optical fiber is surrounded by the fluid rather than air. Thus, compared to a lower fluid level, a higher fluid level would result in a different amount of reflected energy that a sensor detects.

SUMMARY OF THE INVENTION

The invention relates to a non-mechanical fluid level sensor based on light communication channel (LCC) technology. The use of an LCC offers several advantages. For example, the LCC-based fluid detection system of the invention does not require any electrical contact with the fluid and does not contain any moving mechanical parts so wear and tear of the system is minimized or avoided. Various LCC shapes and dimensions can be used. For example, an LCC can be used in the form of a film, sheet, rod, strand, or other structural shapes.

In one aspect of the invention, a fluid level detection system is provided comprising a signal source and an LCC structure that extends into a fluid container. A first end of the LCC structure is connected to the signal source that generates a signal that propagates through the LCC structure. After undergoing multiple internal reflections within the LCC structure, one or more signals reach at least one sensor that is connected to a second end of the LCC structure.

In another aspect of the invention, a fluid level detection system is provided wherein an LCC bus is connected to at least one sensor. The sensor transmits a signal relating to the fluid level via the LCC bus to an electronic system or a display panel of a vehicle. The fluid level detection system includes a signal source and an LCC structure that extends into a fluid container. A first end of the LCC structure is connected to the signal source that generates a signal that propagates through the LCC structure. The at least one sensor is connected to a second end of the LCC structure and receives a signal from the signal source.

The invention is also directed to a fluid level detection system wherein a sensor transmits a signal via an LCC bus to an electronic system, and the electronic system processes the signal relating to the fluid level or transmits the signal relating to the fluid level to another electronic system or a display panel of a vehicle. The fluid level detection system includes a signal source and an LCC structure that extends into a fluid container. A first end of the LCC structure is connected to the signal source that generates a signal that propagates through the LCC structure. At least one sensor that receives a signal from the signal source is connected to a second end of the LCC structure. The at least one sensor is also connected to an LCC bus through which the at least one sensor transmits a signal relating to a fluid level.

The present invention includes various non-limiting embodiments and modifications of the invention several of which are described below.

DETAILED DESCRIPTION OF THE PREFERRED EMBODIMENTS OF THE INVENTION

An LCC, otherwise known as light communication channel, is a structure made of at least one type of light-transmissive material formed into any shape that would allow transmission of a signal in the form of light from one point to another. A signal other than light may originate from a signal source but preferably the signal is converted to light prior to propagation through an LCC using devices such as light emitting diodes. An LCC is described in more detail below, but one of its characteristics is that it can be used as a substrate such as an optical substrate that can be formed into various shapes such as a rectangular slab or the shape of a part or the entirety of, for example, a main frame of an instrument panel display. As such, it can be used as a primary or secondary transmission means for a signal, such as an optical signal propagating from at least one signal source to at least one signal receiver, or it may encompass various electronic and/or optical components to allow a signal such as an optical signal to be directed to various electronic and/or optical components within the LCC substrate, without having to resort to the use of conventional signal focusing means such as a beam splitter or focusing lens. An LCC may also assume other shapes such as a ring, strand, sheet, or ribbon.

As used herein, an LCC structure includes an LCC in the form of sheets, strands, rods, or other structural shapes. An LCC structure also includes an LCC connected or fabricated with one or more parts, components, or systems such as a detector, light source, or an electronic system.

Figure 1:
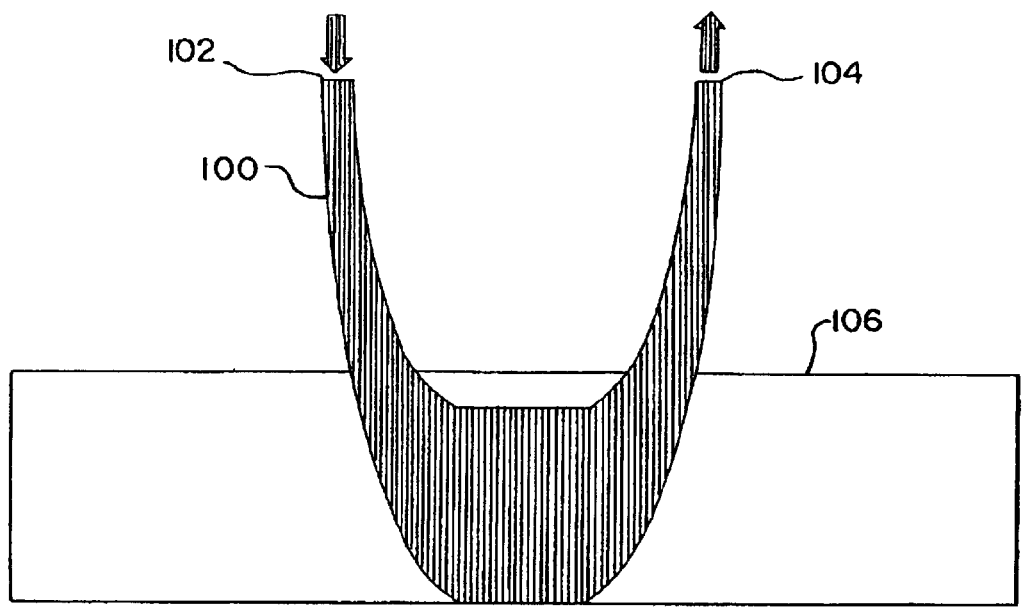
FIG. 1 is an embodiment of the invention that shows an LCC sheet that is partially immersed in a fluid.

FIG. 1 shows an LCC sheet 100, which is connected to a signal source such as a light source on one of the LCC ends 102, and to a sensor on the other end 104. The LCC sheet 100 is dipped into a fluid inside a fluid tank 106. The fluid level is preferably measured by monitoring the intensity of the signal from the light source 102 that reaches the sensor 104. The intensity of light that reaches the sensor 104 depends on the fluid level in the tank. The sensor 104 may be connected to a primary LCC bus through which the sensor can transmit a signal to an electronic system without wiring or other electrical connectors. Thus, the sensor 104 can be used to transmit the information relating to the fluid level to the main console or to a display on the instrument panel. Instead of a signal source or a sensor, a transceiver may be used at one or more ends of an LCC.

Figure 2:
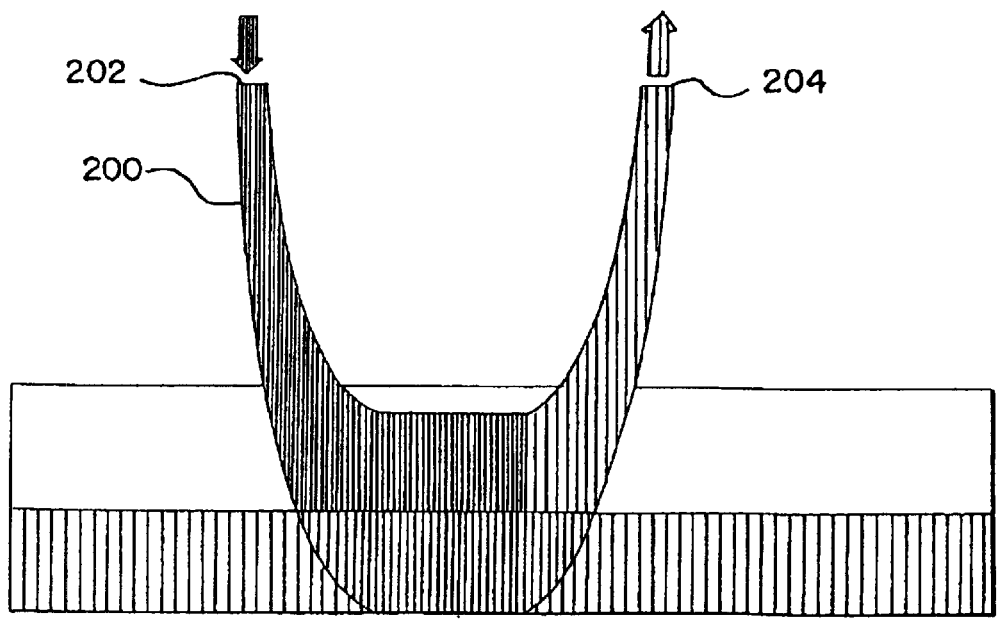
FIG. 2 is the embodiment depicted in FIG. 1 that shows the variation of the intensity of the propagating light from one end of the LCC sheet to the other.

FIG. 2 depicts an LCC sheet in which the intensity of the propagating light is shown to vary along the length of the LCC sheet 200 from one end 202 of the LCC where the light beam enters, to another end 204 where a signal eventually reaches the sensor. As in FIG. 1, one of the ends 202 of the LCC sheet 200 is connected to a signal source while another end 204 is connected to a sensor.

Figure 3:
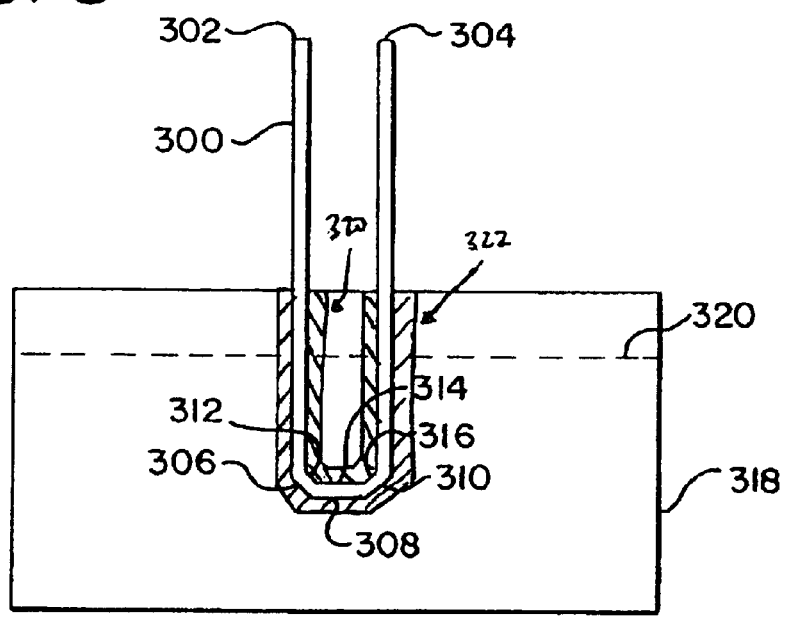
FIG. 3 depicts another embodiment that shows a fluid-level detection system that uses a U-shaped LCC.

FIG. 3 shows another configuration of a fluid-level detection system that utilizes a U-shaped LCC according to the invention. The U-shaped LCC 300, which is partially immersed in a fluid 320, has one end 302 connected to a signal source such as a light source while another end 304 is connected to a sensor. Preferably, at least one of the surfaces 306, 308, 310, 312, 314, 316 at the bottom portion of the LCC is coated with a reflective surface 320 and/or a protective surface 322.

Figure 4:
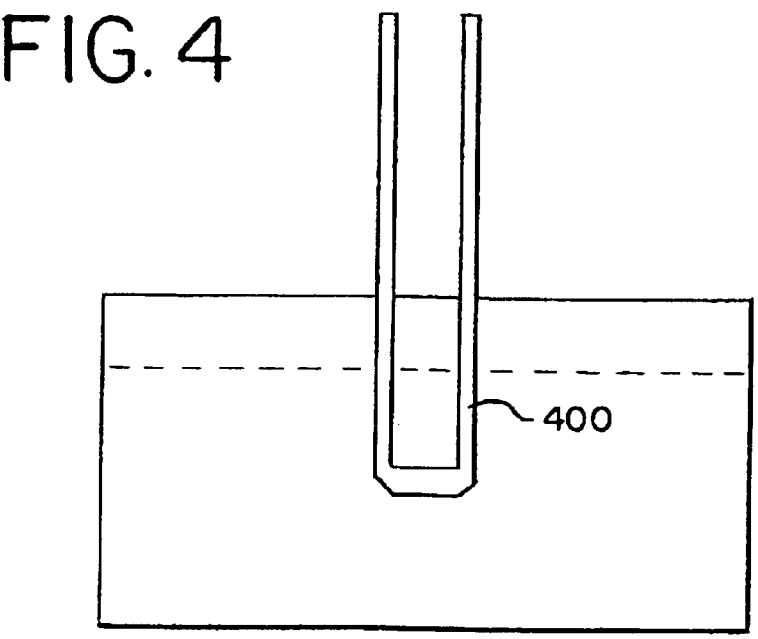
FIG. 4 illustrates another embodiment that shows a fluid-level detection system that uses a U-shaped LCC.

FIG. 4 shows another configuration of a fluid-level detection system of the invention similar to that shown in FIG. 3. A main difference between this detection system and the one shown in FIG. 3 is that the surfaces or portions of the LCC corresponding to 312 and 316 in FIG. 3 are not found in the configuration shown in FIG. 4.

Figure 5:
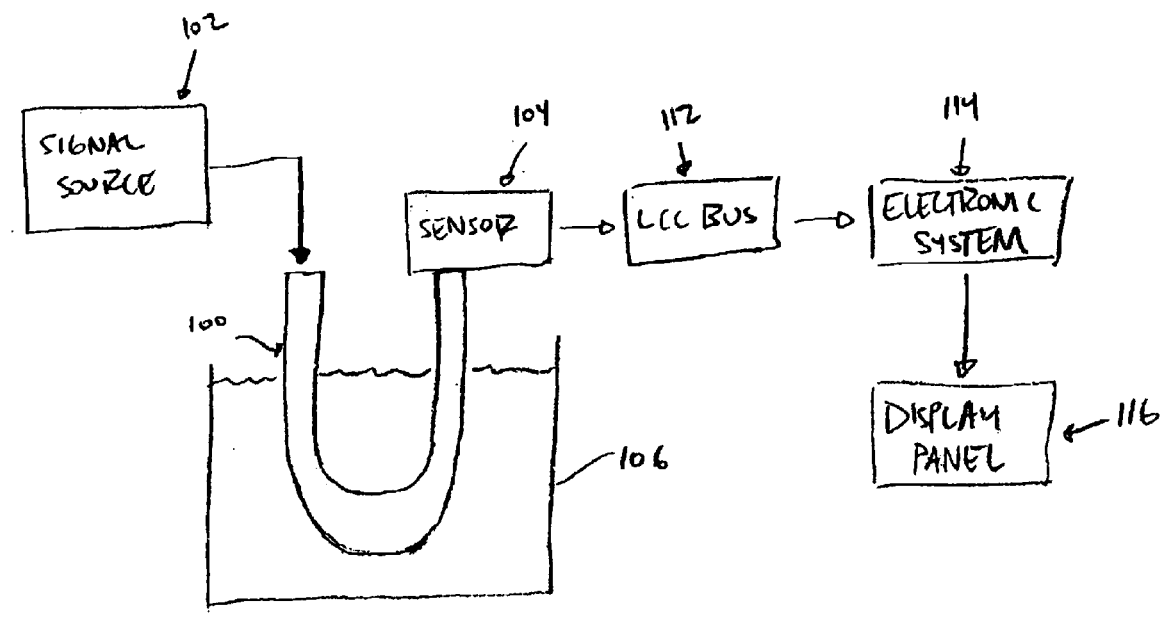
FIG. 5 is a schematic representation of the embodiment shown in FIG. 1 showing the components that send, receive, and process the signal from the LCC structure.

FIG. 5 shows a schematic representation of the LCC sheet 100 and along with the components to provide light into the LCC 100, sense the amount of light exiting the LCC, and transmit the signal to for processing. Specifically, the signal source 102 provides a signal to the LCC 100 a proportion of which reaches the sensor 104 at the output of the LCC 100. The sensor 104 is connected to the primary LCC bus 112 through which the sensor 104 transmits a signal proportional to the amount of light that reached the sensor 104. The signal is transmitted through the LCC bus 112 and reaches the electronic system 114 where it is processed. Optionally, the electronic system 114 may transmit this information to the display panel 116 where it will be visible by the user.

Preferably, a signal source such as an IR laser is used to transmit a signal through the LCC 100, 200, 300, 400. When an IR beam reaches the portion of the LCC 100, 200, 300, 400 immersed in the fluid, the IR beam is partially transmitted into the fluid through the LCC 100, 200, 300, 400 while the IR beam propagates inside the LCC 100, 200, 300, 400. Eventually, a portion of the initial IR beam reaches the sensor 104. The intensity of the IR beam reflected within the LCC 100, 200, 300, 400, or transmitted through the LCC, depends on factors such as the indices of refraction of a given LCC material and the medium surrounding the LCC 100, 200, 300, 400 inside the fluid container.

Preferably, the intensity of a light beam, such as an IR beam, is first measured using an empty fluid container. The intensities of the reflected light at various fluid levels for a given fluid or fluid type inside a tank are then measured. The intensities of the reflected light in an empty and a fluid-containing tank can be used for calibrating or measuring the fuel level in the tank. When the fluid is a solution, a calibration may be performed by measuring the fluid levels in a tank containing only the solvent or solvents contained in the solution.

The index of refraction of the LCC is preferably lower than that of the fluid. However, the refractive indices of a fluid and the LCC material are preferably sufficiently similar such that the detected signal intensity decreases to a very low or undetectable level when the fluid container is full. Ideally, the indices of refraction of the fluid and the LCC material are such that the detected signal intensity reaches a maximum when the fluid container is empty, that is, when the LCC is completely surrounded by air or gas.

A particular light polarization of the signal beam may be used to enhance or optimize the accuracy of fluid level detection.

Suitable coatings may be applied to the surface of an LCC structure to make it resistant to adverse reactions involving the LCC structure material and the fluid or contaminants present in the fluid. Preferably, the applied coating does not adversely affect the performance of the LCC-based fluid-level detection system. Because the presence of a film on an LCC surface can degrade the performance of the fluid level detection system, the applied coating preferably also prevents the formation of a film on the surface of the LCC. In one aspect of the invention, the applied coating repels the fluid or other components present in the fluid. For example, if the fluid to be monitored is mainly nonpolar or contains mainly organic compounds, the LCC surface may be coated with a lipophobic or a hydrophilic substance to minimize or prevent the formation of a film on the surface of the LCC.

An LCC can be fabricated using one or more materials that permit light of various wavelengths to pass or diffuse through the material. Preferably, the LCC material used is one that allows the measured reflected light intensity to vary more or less linearly with the fluid level in the container.

An LCC may comprise one or more transparent or translucent materials. Thus, the LCC may comprise a first material transparent or translucent to a first wavelength of one or more signals and a second material transparent or translucent to a second wavelength of the one or more signals.

An LCC can also be fabricated using a polymeric material. In particular, an LCC can be prepared using polyethylene terephthalate, polypropylene, polyethylene, polyisobutylene, polyacrylonitrile, poly(vinyl chloride), poly(methyl metacrylate), silica, or polycarbonate.

An LCC may have various configurations such as flat, curvilinear, wavy, and asymmetrical. Thus, a thin sheet or film of LCC may be used as a light or signal propagation medium. A particularly suitable LCC configuration is one that allows a measurable reflected signal or light intensity to be detected over an entire range of fluid levels. Preferably, the LCC configuration permits a more or less linear variation of the measured reflected light intensity with the fluid level. In addition to having various configurations, an LCC may also have varying dimensions such as thickness and width.

An LCC is preferably made of a moldable material so it can be flexed or formed to a desired shape. Thus, for example, the LCC may have parts or areas that are connected onto a surface of a PC board. The LCC can be connected to or integrated with structures such as printed circuit boards, flexible substrates, flatwire, and MID circuits.

An LCC may also have a reflective or absorptive coating on one or more surfaces, preferably at one or more ends of the LCC. In one aspect of the invention, several LCC structures are separated by or connected via a reflective or absorptive material. The reflective or absorptive coating may cover at least one surface of the LCC. Alternatively, the reflective or absorptive coating may cover the entire surface or substantially the entire surface of the LCC except for parts of the surface where the signal source and detector are connected to the LCC.

The selected reflective coating is preferably one that enhances the measurable intensity of the reflected light that reaches the detector. A highly suitable reflective material is one that allows the intensity of the detected reflected light to vary linearly with the fluid level in the container. The reflective coating may comprise any material that reflects signals within the LCC. Suitable reflective coatings include metals or metallic alloys containing aluminum, copper, silver, gold, and other metals.

An LCC structure may be positioned in any suitable location within the fluid container. Thus, the LCC structure may be placed against the container wall or in other suitable areas inside the fluid container.

The signal source and sensors are preferably operatively connected to one or more surfaces or ends of the LCC. As used herein, "operatively connected" includes the formation of an optical, electrical, or other interface for transmitting and receiving the signals through the LCC, as well as attachment configurations, attachment substances, other attachment mechanisms, or a combination of these materials for affixing the signal sources and the detectors onto the LCC. The attachment configurations include physical adaptations of the LCC such as an indentation or a pressure fit structure. The attachment substances include adhesives, resins, and solder.

A signal source and a sensor may be integrated into a component such as an RF transceiver, which may transmit a first signal at a given time and receive a second signal at another time. The first and second signals may have the same or different frequencies.

In the various aspects of the invention, each signal source transmits one or more signals through the LCC to one or more sensors. Preferably, a signal source transmits one or more signals in response to an input signal from an electronic system. The signal source may transmit one or more continuous, pulsed, or a combination of continuous and pulsed signals.

An ideal signal source is a light source. Preferably, the signal source is an infrared light source. At least one signal source transmits one or more signals through the LCC. The signal source also includes, but is not limited to, a visible light source or an ultraviolet light source. In one aspect of the invention, at least one signal source is a visible light generation device such as a light emitting diode (LED). In another aspect, each signal source is a radio frequency (RF) generation device such as an RF transmitter. In still another aspect, a first signal source is an electromagnetic radiation generation device such as a green LED and the second signal source is another electromagnetic radiation generation device such as a blue or infrared LED.

A signal from a signal source may be of any electromagnetic frequency capable of transmission through the LCC between a signal source and a sensor. The signal may also be a combination of electromagnetic frequencies. The signal may be modulated or coded, and they may propagate along the same or opposite directions. Preferably, the signal is capable of essentially diffusing throughout the entire volume of the LCC. As used herein, "essentially diffusing" includes the propagation of a signal in various directions within the LCC unless the signal source or another component blocks the signal, or the surface of the LCC reflects the signal.

A signal such as an optical signal from optoelectronic transmitters can be channeled or transported through air if there are no obstacles in their path of travel. Preferably, the transmitters generate a unique wavelength of light. A wavelength selective filter may be placed in front of the detector so there is little or no interference between different transmitters and detectors. In one aspect, communication through the air is achieved using a single wavelength of light as a signal and incorporating a code before each signal so only the designated detector or detectors will recognize the code and respond to the signal.

A sensor may comprise one or more detectors. The detectors may receive or collect one or more signals from the LCC. Preferably, the detectors provide an output signal to at least one electronic system. The detectors may have one or more frequency specific filters to reduce or eliminate interference from signals with undesired frequencies. The frequency specific filter selectively allows a particular detector to receive a signal having a particular frequency or narrow range of frequencies.

A detector may be a photodetector or an RF detector. The detector includes, but is not limited to, photodiodes, microchannel plates, photomultiplier tubes, or combination of detectors.

In one aspect of the invention, a sensor communicates remotely without any wiring through an LCC bus. The sensor may transmit information relating to the fluid level to an electronic component or system such as a main console or an instrument panel display of a vehicle. One or more sensors may be positioned in any suitable location on the surface of the LCC to receive one or more signals. Multiple sensors may receive signals from a single signal source.

The fluid-level detection system of the invention may be used to monitor the fluid level in containers of varying sizes such as a large tank or a small fluid reservoir. Two or more fluid-level detection systems may be connected to a single electronic system, such as a process control electronics. The use of two or more fluid-level detection systems allows simultaneous and convenient monitoring of the fluid levels in several tanks or containers.

The fluid detection system is preferably used to monitor the fluid level in a fuel tank of an automobile or other vehicles, including air and water vehicles. The fluid level detection system of the invention may also be used for other applications such as in agricultural, pharmaceutical, and cosmetic industries. The fluid level or volume of various types of fluids may be monitored. Thus, the fluids to be monitored include, but are not limited to, liquid fuels, colloids, emulsions, organic or aqueous solvents, solutions, and other types of mixtures.

Various embodiments of the invention have been described and illustrated. However, the description and illustrations are by way of example only. Other embodiments and implementations are possible within the scope of this invention and will be apparent to those of ordinary skill in the art. Therefore, the invention is not limited to the specific details, representative embodiments, and illustrated examples in this description. Accordingly, the invention is not to be restricted except as necessitated by the accompanying claims and their equivalents.

What is claimed is:

1. A fluid level detection system comprising:

a signal source, an LCC structure that extends into a fluid container with a first end of the LCC structure being connected to the signal source, wherein the LCC structure is polyethylene terephthalate, polypropylene, polyethylene or polycarbonate, and the LCC structure is formed as a thin sheet, and at least one sensor that receives a signal from the signal source and is connected to a second end of the LCC structure, wherein a signal from the signal source propagates through the LCC structure.

2. The fluid level detection system of claim 1, wherein the signal source is an infrared light source, visible light source, ultraviolet light source, an LED, or an RF source.

3. The fluid level detection system of claim 1, wherein the indices of refraction of an LCC material and a fluid inside a fluid container give rise to a negligible signal intensity that reaches the at least one sensor when the fluid container is full.

4. The fluid level detection system of claim 1, wherein the at least one sensor transmits a signal relating to a fluid level through an LCC bus.

5. The fluid level detection system of claim 1, wherein the at least one sensor transmits a signal to an electronic system or a display panel of a vehicle.

6. The fluid level detection system of claim 1, wherein a surface of the LCC structure is coated with a reflective or a protective coating.

7. A fluid level detection system comprising:

a signal source, an LCC structure that extends into a fluid container with a first end of the LCC structure being connected to the signal source, and through which a signal from the signal source propagate, wherein the LCC structure is polyethylene terephthalate, polypropylene, polyethylene or polycarbonate, and the LCC structure is formed as a thin sheet, at least one sensor that is connected to a second end of the LCC structure and that receives a signal from the signal source, and an LCC bus to which the at least one sensor is connected, and wherein the at least one sensor transmits a signal via the LCC bus to an electronic system or a display panel of a vehicle.

8. The fluid level detection system of claim 7, wherein the signal source is an infrared light source, visible light source, ultraviolet light source, an LED, or an RF source.

9. The fluid level detection system of claim 7, wherein the indices of refraction of an LCC material and a fluid inside a fluid container give rise to a negligible signal intensity that reaches the at least one sensor when the fluid container is full.

10. The fluid level detection system of claim 7, wherein a surface of the LCC structure is coated with a reflective or a protective coating.

11. A fluid level detection system comprising:

a signal source, an LCC structure that extends into a fluid container, with a first end of the LCC structure being connected to the signal source, and through which a signal from the signal source propagates, wherein the LCC structure is polyethylene terephthalate, polypropylene, polyethylene or polycarbonate, and the LCC structure is formed as a thin sheet, at least one sensor connected to a second end of the LCC, wherein the at least one sensor receives a signal that propagates through the LCC, and an LCC bus connected to the at least one sensor to which the at least one sensor transmits a signal relating to a fluid level, wherein the at least one sensor transmits a signal via an LCC bus to an to an electronic system, and the electronic system processes the signal relating to the fluid level or transmits the signal relating to the fluid level to another electronic system or a display panel of a vehicle.

12. The fluid level detection system of claim 11, wherein the signal source is an infrared light source, visible light source, ultraviolet light source, an LED, or an RF source.

13. The fluid level detection system of claim 11, wherein the indices of refraction of an LCC material and a fluid inside a fluid container give rise to a negligible signal intensity that reaches the at least one sensor when the fluid container is full.

* * * * *

UNITED STATES PATENT AND TRADEMARK OFFICE
CERTIFICATE OF CORRECTION

PATENT NO. : 6,949,758 B2  Page 1 of 1
APPLICATION NO. : 10/265954
DATED : September 27, 2005
INVENTOR(S) : Zhong-You Shi et al.

It is certified that error appears in the above-identified patent and that said Letters Patent is hereby corrected as shown below:

On the Title Page

Item (54), Title, delete "LCC-BASED" and substitute --LIGHT COMMUNICATION CHANNEL-BASED-- in its place.

Page 2, in column 1, line 28, under "U.S. DOCUMENTS", delete "Schäpörkotter" and substitute --Shäperkötter-- in its place.

In column 1, lines 1-2, in the title, delete "LCC-BASED" and substitute --LIGHT COMMUNICATION CHANNEL-BASED-- in its place.

Signed and Sealed this

Twenty-fourth Day of April, 2007

JON W. DUDAS
*Director of the United States Patent and Trademark Office*